United States Patent
Helland et al.

(10) Patent No.: US 6,748,268 B1
(45) Date of Patent: Jun. 8, 2004

(54) THREE LEAD UNIVERSAL PACING AND SHOCKING SYSTEM

(75) Inventors: John R. Helland, Saugus, CA (US); Gene A. Bornzin, Simi Valley, CA (US); Eric Falkenberg, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 329 days.

(21) Appl. No.: 09/945,079

(22) Filed: Aug. 31, 2001

(51) Int. Cl.<sup>7</sup> ............................................. A61N 1/368
(52) U.S. Cl. ........................................................ 607/4
(58) Field of Search .................................. 600/373, 374, 600/393, 508, 509; 607/4, 5, 9, 119, 122, 123

(56) References Cited

U.S. PATENT DOCUMENTS

| | | | |
|---|---|---|---|
| 4,548,203 A | 10/1985 | Tacker, Jr. et al. | 128/419 D |
| 4,932,407 A * | 6/1990 | Williams | 128/419 D |
| 5,111,811 A | 5/1992 | Smits | 128/419 D |
| 5,174,289 A | 12/1992 | Cohen | 128/419 PG |
| 5,235,978 A * | 8/1993 | Hirschberg et al. | 607/5 |
| 5,267,560 A | 12/1993 | Cohen | 607/25 |
| 5,314,430 A | 5/1994 | Bardy | 607/5 |
| 5,350,404 A | 9/1994 | Adams et al. | 607/5 |
| 5,366,494 A | 11/1994 | Holleman et al. | 607/119 |
| 5,411,524 A | 5/1995 | Rahul | 607/4 |
| 5,411,529 A | 5/1995 | Hudrlik | 607/5 |
| 5,423,865 A | 6/1995 | Bowald et al. | 607/5 |
| 5,431,683 A * | 7/1995 | Bowald et al. | 607/5 |
| 5,466,254 A | 11/1995 | Helland | 607/123 |
| 5,531,764 A | 7/1996 | Adams et al. | 607/5 |
| 5,545,204 A | 8/1996 | Cammilli et al. | 607/123 |
| 5,662,697 A | 9/1997 | Li et al. | 607/122 |
| 5,720,768 A * | 2/1998 | Verboven-Neilissen | 607/9 |
| 5,800,465 A | 9/1998 | Thompson et al. | 607/9 |
| 5,814,079 A | 9/1998 | Kieval | 607/4 |

(List continued on next page.)

FOREIGN PATENT DOCUMENTS

| | | | |
|---|---|---|---|
| EP | 0813889 A2 | 12/1997 | A61N/1/368 |
| WO | WO 00/33914 | 6/2000 | A61N/1/368 |

*Primary Examiner*—Jeffrey R. Jastrzab
*Assistant Examiner*—Frances P. Oropeza

(57) ABSTRACT

A three lead implantable cardiac stimulation system is capable of delivering stimulation pulses to any one chamber or combination of chambers of a heart. The system includes a first lead for implant in the right ventricle and having a right ventricular defibrillation electrode, a second lead for implant in the coronary sinus and having a left ventricular defibrillation electrode, and a third lead for implant in the coronary sinus and having a left atrial defibrillation electrode. One of the leads further including a right atrial defibrillation electrode for placement in one of the right atrium and superior vena cava. The system further includes an implantable cardiac stimulation device including a programmable pulse generator that delivers defibrillation pulses to any one of the defibrillation electrodes or to any combination of the defibrillation electrodes. The leads may further provide at least one pacing electrode for each chamber of the heart and the device is programmable to provide pacing pulses to any one of the pacing electrodes.

17 Claims, 2 Drawing Sheets

U.S. PATENT DOCUMENTS

| | | |
|---|---|---|
| 5,814,081 A | 9/1998 | Ayers et al. .................... 607/5 |
| 5,836,975 A | 11/1998 | DeGroot ........................ 607/5 |
| 5,836,976 A | 11/1998 | Min et al. ....................... 607/6 |
| 5,865,838 A | 2/1999 | Obel et al. ...................... 607/5 |
| 5,902,324 A | 5/1999 | Thompson et al. ............. 607/9 |
| 5,902,329 A | 5/1999 | Hoffmann et al. ........... 607/121 |
| 5,913,887 A | 6/1999 | Michel ........................ 607/123 |
| 5,935,159 A | 8/1999 | Cross, Jr. et al. ............ 607/116 |
| 5,964,795 A | 10/1999 | McVenes et al. ............ 607/122 |
| 5,968,079 A | 10/1999 | Warman et al. ................ 607/5 |
| 5,978,704 A | 11/1999 | Ideker et al. ................... 607/5 |
| 5,987,354 A | 11/1999 | Cooper et al. .................. 607/5 |
| 5,999,853 A | 12/1999 | Stoop et al. .................... 607/9 |
| 6,006,131 A | 12/1999 | Cooper et al. .................. 607/5 |
| 6,041,256 A | 3/2000 | Michel ........................... 607/5 |
| 6,055,457 A | 4/2000 | Bonner ....................... 607/126 |
| 6,067,471 A | 5/2000 | Warren .......................... 607/5 |
| 6,070,100 A | 5/2000 | Bakels et al. ................... 607/9 |
| 6,070,101 A | 5/2000 | Struble et al. .................. 607/9 |
| 6,070,104 A | 5/2000 | Hine et al. ................... 607/123 |
| 6,081,748 A | 6/2000 | Struble et al. .................. 607/9 |
| 6,122,545 A | 9/2000 | Struble et al. .................. 607/9 |
| 6,169,921 B1 | 1/2001 | KenKnight et al. ............. 607/4 |
| 6,205,357 B1 | 3/2001 | Ideker et al. .................. 607/14 |
| 6,249,700 B1 | 6/2001 | Alt ................................. 607/4 |
| 6,249,709 B1 | 6/2001 | Conger et al. ............... 607/122 |
| 6,266,563 B1 | 7/2001 | KenKnight et al. ............. 607/5 |
| 6,339,724 B1 | 1/2002 | Thong .......................... 607/28 |
| 6,434,428 B1 | 8/2002 | Sloman et al. ................ 607/28 |
| 6,434,430 B2 * | 8/2002 | Borgersen ................... 607/122 |
| 6,456,881 B1 | 9/2002 | Bornzin et al. ............... 607/27 |
| 6,490,486 B1 | 12/2002 | Bradley ........................ 607/28 |
| 6,490,489 B2 | 12/2002 | Bornzin et al. ............. 607/122 |
| 6,493,583 B1 | 12/2002 | Levine et al. .................. 607/9 |
| 6,587,720 B2 * | 7/2003 | Hsu et al. ....................... 607/4 |
| 2002/0103507 A1 | 8/2002 | Helland ......................... 607/5 |
| 2003/0023271 A1 | 1/2003 | Hsu et al. ....................... 607/4 |

* cited by examiner

THREE LEAD UNIVERSAL PACING AND SHOCKING SYSTEM

CROSS-REFERENCE TO RELATED APPLICATIONS

This application is related to, commonly-assigned U.S. patent applications: Ser. No. 09/910,154, filed Jul. 19, 2001, titled TWO LEAD UNIVERSAL DEFIBRILLATION SYSTEM, now abandoned; Ser. No. 09/944,678, filed Aug. 31, 2001, titled IMPLANTABLE CARDIAC LEAD FOR SHOCKING, PACING AND SENSING WITHIN THE LEFT HEART AND SYSTEM; Ser. No. 09/945,449, filed Aug. 31, 2001, titled TWO LEAD UNIVERSAL DEFIBRILLATION, PACING AND SENSING SYSTEM; Ser. No. 09/945,415, filed Aug. 31, 2001, titled CORONARY SINUS LEAD FOR STIMULATING AND SENSING IN THE RIGHT AND LEFT HEART AND SYSTEM; Ser. No. 09/944,683, filed Aug. 31, 2001, titled CORONARY SINUS CARDIAC LEAD FOR STIMULATING AND SENSING THE ATRIA OF THE RIGHT AND LEFT HEART AND SYSTEM; and Ser. No. 09/945,417, filed Aug. 31, 2001, titled TWO LEAD CARDIAC STIMULATION SYSTEM THAT PACES ALL FOUR HAMBERS OF A HEART.

FIELD OF THE INVENTION

The present invention generally relates to an implantable cardiac stimulation system and more particularly to a three lead universal defibrillation and pacing system capable of providing defibrillating and pacing pulses to all four chambers of the heart. The present invention is further directed to such a system having two leads implantable in the coronary sinus region of the heart to permit implementation of the universal defibrillation and pacing system.

BACKGROUND OF THE INVENTION

Implantable cardiac stimulation devices are well known in the art. Such devices may include, for example, implantable cardiac pacemakers and defibrillators. The devices are generally implanted in a pectoral region of the chest beneath the skin of a patient within what is known as a subcutaneous pocket. The implantable devices generally function in association with one or more electrode carrying leads which are implanted within the heart. The electrodes are usually positioned within the right side of the heart, either within the right ventricle or right atrium, or both, for making electrical contact with their respective heart chamber. Conductors within the leads and a proximal connector carried by the leads couple the electrodes to the device to enable the device to sense cardiac electrical activity and deliver the desired therapy.

Traditionally, therapy delivery had been limited to the venous, or right side of the heart. The reason for this is that implanted electrodes can cause blood clot formation in some patients. If a blood clot were released arterially from the left heart, as for example the left ventricle, it could pass directly to the brain potentially resulting in a paralyzing or fatal stroke. However, a blood clot released from the right heart, as from the right ventricle, would pass into the lungs where the filtering action of the lungs would prevent a fatal or debilitating embolism in the brain.

Recently, new lead structures and methods have been proposed and even practiced for delivering cardiac rhythm management therapy to the left heart. These lead structures and methods avoid direct electrode placement within the left atrium and left ventricle of the heart by lead implantation within the coronary sinus region of the heart. As used herein, the phrase "coronary sinus region" refers to the venous vasculature of the left ventricle, including any portions of the coronary sinus, great cardiac vein, left marginal vein, left posterior ventricular vein, middle cardiac vein, and/or small cardiac vein or any other cardiac vein accessible by the coronary sinus.

It has been demonstrated that electrodes placed in the coronary sinus region of the heart may be used for left atrial pacing, left ventricular pacing, or cardioversion and defibrillation. These advancements enable implantable cardiac stimulation devices to address the needs of a patient population with left ventricular dysfunction and/or congestive heart failure which would benefit from left heart side pacing, either alone or in conjunction with right heart side pacing (bi-chamber pacing), and/or defibrillation.

Universal pacing and/or defibrillation systems capable of pacing and/or defibrillating all of the chambers of the right and left heart would of course require numerous pacing and/or defibrillation electrodes to be employed within the heart and its coronary venous system. Providing the numerous electrodes to implement such universal heart stimulation systems would in turn require an inordinate number of leads if currently available right and left heart leads were employed. This would result in unduly long implant procedures and possibly more leads than the human anatomy is able to accommodate. The number of leads required may also make it difficult to accurately locate each electrode at its most efficacious position within the heart.

Hence, there is a need in the art for new and improved right and left heart leads and lead configurations which provide efficient left heart access and integrated right and left heart therapies. Electrode placement on the leads should enable effective therapy and electrode selection to accommodate differences in heart physiology from one patient to another. Universal pacing and defibrillation systems that would result from the new and improved leads and lead configurations could provide significant improved therapies. Coordinated right heart and left heart pacing therapies would be made possible. Further, improved defibrillation therapies would also be made possible. The therapies could provide improved electrode configuration selection for improved defibrillation energy distribution within the heart or support improved sequential defibrillation pulse techniques. The present invention is directed to left heart leads and right and left heart lead configurations which address the above mentioned needs.

SUMMARY OF THE INVENTION

The invention provides an implantable cardiac stimulation system for delivering stimulation pulses to any one chamber or combination of chambers of a heart. The system includes a lead system consisting of a first lead for implant in the right ventricle and having a right ventricular defibrillation electrode, a second lead for implant in the coronary sinus and having a left ventricular defibrillation electrode for placement in electrical contact with the left ventricle adjacent to the left ventricle and within the coronary sinus, and a third lead for implant in the coronary sinus and having a left atrial defibrillation electrode for placement in electrical contact with the left atrium adjacent to the left atrium and within the coronary sinus. One of the leads further includes a right atrial defibrillation electrode for placement in one of the right atrium and superior vena cava. The system further includes an implantable cardiac stimulation device including a programmable pulse generator that delivers defibrillation pulses to any one of the defibrillation electrodes or to any combination of the defibrillation electrodes.

In accordance with further aspects of the invention, the first lead may include a right ventricular pacing electrode or bipolar electrode pair and the pulse generator is programmable to deliver pacing pulses to the right ventricular pacing electrode or bipolar electrode pair. The second lead further include a left ventricular pacing electrode or bipolar electrode pair for placement in electrical contact with the left ventricle and the pulse generator is programmable to deliver pacing pulses to the left ventricular pacing electrode or bipolar electrode pair. The third lead may further include at least one left atrial pacing electrode for placement in electrical contact with the left atrium and the pulse generator is programmable to deliver pacing pulses to the at least one left atrial pacing electrode. The third lead may still further include at least one right atrial pacing electrode for placement in electrical contact with the right atrium and the pulse generator is programmable to deliver pacing pulses to either one or both of the atrial pacing electrodes. The atrial pacing electrodes are preferably spaced apart on the lead so that when the left atrial pacing electrode is in electrical contact with and adjacent the left atrium within the coronary sinus, the at least one right atrial pacing electrode is in electrical contact with the right atrium and adjacent to the ostium of the coronary sinus within the coronary sinus.

In accordance with still further aspects of the invention, the defibrillation electrodes are preferably coil electrodes. The device may further include a conductive case and the pulse generator may be programmable to deliver stimulation pulses between any one of the defibrillation electrodes and the case.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Exemplary Embodiment of the Invention

Figure 1:
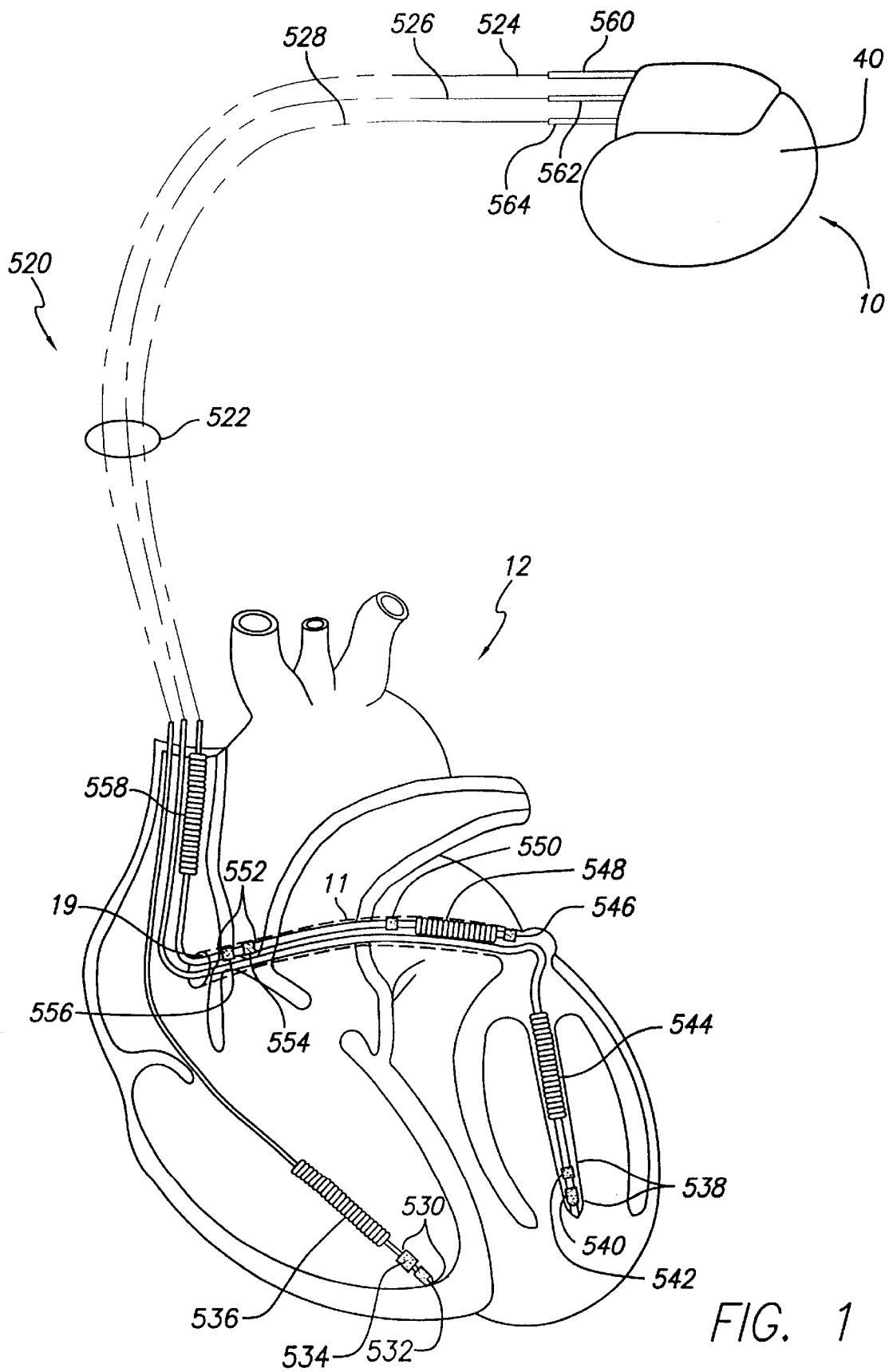
FIG. 1 is a simplified diagram illustrating a three lead implantable universal cardiac stimulation system embodying the present invention capable of delivering both pacing and defibrillation pulses to all four chambers of the heart.

FIG. 1 shows a three lead implantable cardiac stimulation system 520 embodying the present invention capable of providing universal pacing and defibrillation therapy to the heart 12. More specifically, the system 520 of FIG. 1 is capable of delivering stimulation pulses to any one chamber or combination chambers of the heart. The system 520 generally includes an implantable cardiac stimulation device 10 and a lead system 522. The lead system 522 includes a first lead 524 configured for implant in the right ventricle, a second lead 526 configured for implant in the coronary sinus 11 of the left heart, and a third lead 528 which is a dedicated atrial lead also configured for implant in the coronary sinus 11 of the heart.

The lead 524 includes a right ventricular bipolar sensing and pacing electrode pair 530 including a right ventricular tip electrode 532 and a right ventricular bipole electrode 534. Lead 524 also includes a right ventricular defibrillation coil electrode 536. The electrodes are spaced on the lead 524 such that when the bipolar electrode pair 530 is within the apex of the right ventricle as illustrated, the right ventricular defibrillation coil electrode 536 is within the right ventricle.

Lead 526 includes a left ventricular bipolar sensing and pacing electrode pair 538 including a left ventricular tip electrode 540 and a left ventricular bipole electrode 542. Lead 526 further includes a left ventricular defibrillation coil electrode 544. The electrodes are spaced on lead 526 such that when the left ventricular bipolar electrode pair 538 is at the apex of the heart in electrical contact with and adjacent to the left ventricle within the coronary sinus 11, the left ventricular defibrillation coil electrode 544 is in electrical contact with and adjacent to the left ventricle within the coronary sinus 11.

Lead 528 includes, from its distal end towards its proximal end, a distal left atrial sensing and pacing electrode 546, a left atrial defibrillation coil electrode 548, a proximal left atrial sensing and pacing electrode 550, a right atrial bipolar sensing and pacing electrode pair 552 including sensing and pacing electrode 554 and sensing and pacing electrode 556, and a right atrial defibrillation coil electrode 558. The electrodes are spaced along lead 528 such that when the distal left atrial sensing and pacing electrode 546 is in electrical contact with and adjacent the left atrium within the coronary sinus 11, the left atrial defibrillation coil electrode 548 is in electrical contact with and adjacent the left atrium within the coronary sinus 11, the proximal left atrial sensing and pacing electrode 550 is in electrical contact with and adjacent the left atrium within the coronary sinus 11, the right atrial bipolar electrodes ;554 and 556 are in electrical with and adjacent the right atrium within the coronary sinus 11 and adjacent the coronary sinus ostium 19 and the right atrial defibrillation coil electrode 558 is within the superior vena cava and/or the right atrium of the heart.

The leads 524, 526, and 528 each includes a proximal connector 560, 562, and 564, respectively. The connectors are arranged to be received by the device 10 for coupling the electrodes of the leads to the internal circuitry of the device 10. More specifically, when lead 524 is coupled to the device by the connector 560, and with reference to FIG. 2, the right ventricular tip electrode 532 is coupled to the right ventricular tip terminal 47, the right ventricular bipole electrode 534 is coupled to the right ventricular ring terminal 48, and the right ventricular defibrillation coil electrode 536 is coupled to the right ventricular coil terminal 46. When lead 526 is coupled to the device 10 by the connector 562, the left ventricular tip electrode 540 is coupled to the left ventricular tip terminal 55, the left ventricular bipole electrode 542 is coupled to the left ventricular ring terminal 56, and the left ventricular defibrillation coil electrode 544 is coupled to the left ventricular coil terminal 54. When lead 528 is coupled to the device by connector 564, the left atrial sensing and pacing electrode 546 is coupled to the left atrial tip terminal 51, the left atrial defibrillation coil electrode 548 is coupled to the left atrial coil terminal 50, the left atrial sensing and pacing electrode 550 is coupled to the left atrial ring terminal 52, the right atrial sensing and pacing electrode 554 is coupled to the right atrial tip terminal 43, the right atrial sensing and pacing electrode 556 is coupled to the right atrial ring terminal 44, and the right atrial defibrillation coil electrode 558 is coupled to the SVC coil terminal 42.

With specific regard to the bipolar electrode pair 552, electrodes 554 and 556 are positioned on the lead 526 such that the most proximal one of electrodes 554 and 556, namely, electrode 556, is adjacent the ostium 19 of the coronary sinus 11 within the coronary sinus 11. With the bipolar electrode pair 552 thus placed, electrodes 554 and 556 are in electrical contact with and adjacent the right atrium for providing effective right atrial pacing.

The system 520 is truly a universal cardiac stimulation system. Numerous different electrode configurations for providing both pacing and defibrillations are rendered possible. For example, any one of the sensing and pacing electrodes may be utilized along with the conductive case 40 of the device 10 for unipolar pacing of its respective chamber. Further, each chamber may be paced in a bipolar mode. The right ventricle may be paced utilizing the bipolar electrode pair 530, the right atrium may be bipolar paced using the bipolar electrode pair 552, and the left ventricle may be bipolar paced using the bipolar pair 538. The left atrium may be bipolar paced by either using electrode 546 with the defibrillation coil electrode 548 or with the electrode 550 with the defibrillation coil 548. Because electrode 546 is distal to the defibrillation coil electrode 548 and the electrode 550 is proximal to the defibrillation coil electrode 548, different combinations of electrodes may be utilized to suit a particular physiology of the patient's heart to provide a best fit for the patient.

With respect to defibrillation, any one of the defibrillation coil electrodes may be utilized to apply defibrillation stimulation pulses with the conductive case 40 of the device 10. Still further, any combination of the defibrillation coil electrodes 536, 558, 544, and 548 may be utilized for defibrillating the heart. For example, the electrode configuration of the right atrial defibrillation coil electrode 558 and the left atrial defibrillation coil electrode 548 may render the most effective atrial defibrillation therapy. Further, the defibrillation electrodes need not be coil electrodes but could take other forms as known in the art.

Particular note may be made to lead 526 in that it is a dedicated atrial lead and has utility in and of itself for providing right atrial pacing therapy, left atrial pacing therapy, and atrial defibrillation therapy. Moreover, lead 528 provides bipolar pacing of the right atria and two different electrode configurations for bipolar pacing of the left atrium.

The implantable cardiac stimulation system 520 of FIG. 1 may be utilized to further advantage in restoring homogeneity to the electrical activation sequence of the atria of the heart 12. In a healthy heart, right atrial activation precedes left atrial activation by about 70 to 130 milliseconds. Hence, in a sick heart which does not have such atrial activation sequencing, the right atria may be paced 70 to 130 milliseconds before the left atrium is paced to return homogeneity of atrial activations to the heart.

An Exemplary Cardiac Stimulation Device

Figure 2:
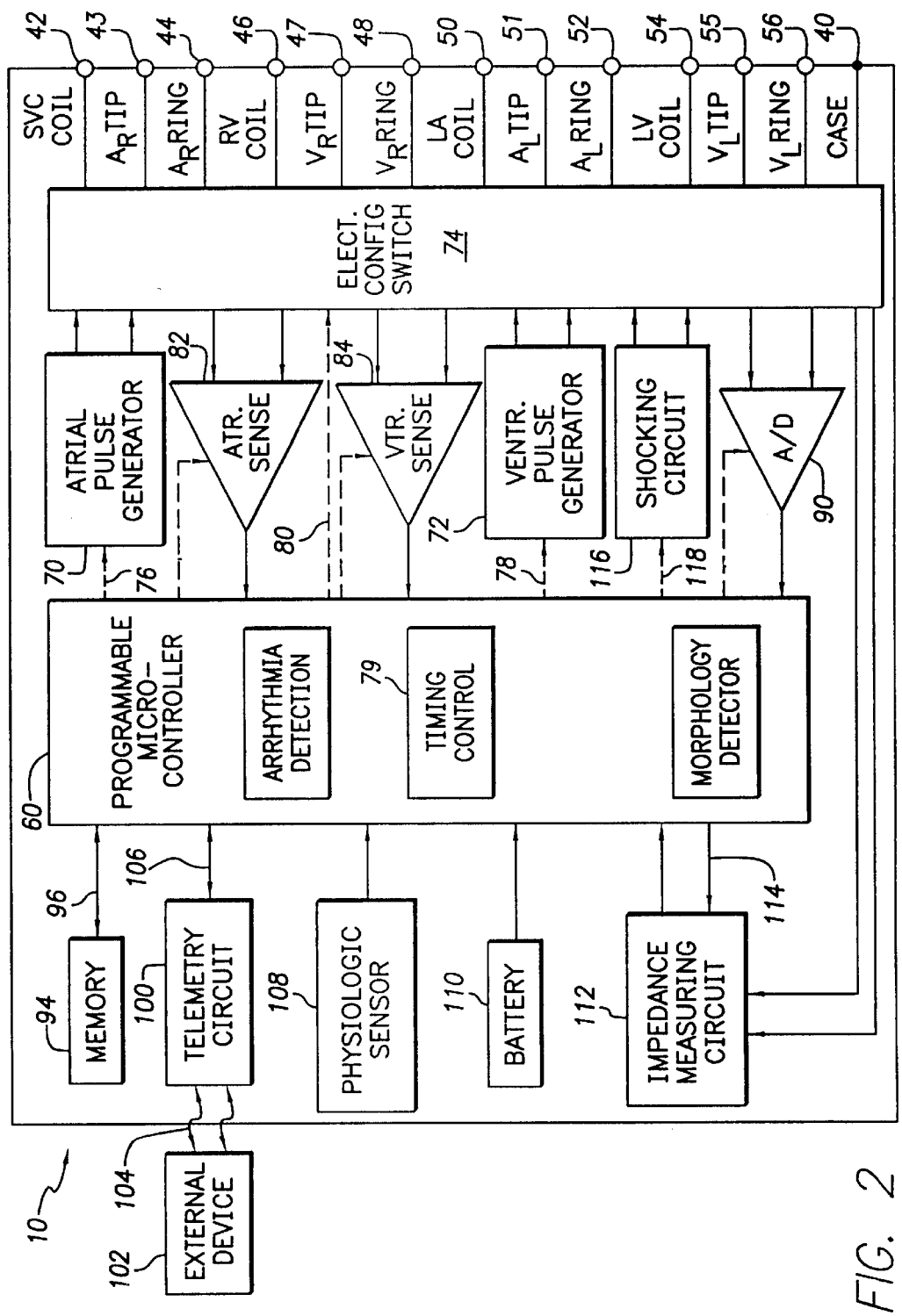
FIG. 2 is a functional block diagram of a multi-chamber implantable stimulation device which may be employed in the system of FIG. 1 which can provide cardioversion, defibrillation and pacing stimulation for all four chambers of the heart.

As illustrated in FIG. 2, a simplified block diagram is shown of a multi-chamber implantable stimulation device 10 which may be employed to advantage in the system of FIG. 1. The device is capable of treating arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber (s) with cardioversion, defibrillation and pacing stimulation.

The housing 40 for the stimulation device 10, shown schematically in FIG. 2, is often referred to as the "can", "case" or "case electrode" and may be programmably selected to act as a return stimulation electrode for all "unipolar" pacing modes. The housing 40 may further be used as a return electrode alone or in combination with one or more of the coil electrodes, 536, 538, 544, and 548 (FIG. 1), for shocking purposes. The housing 40 further includes a connector (not shown) having a plurality of terminals, 42, 43, 44, 46, 47, 48, 50, 51, 52, 54, 55, and 56 (shown schematically and, for convenience, the names of the electrodes to which they may be connected as appropriate are shown next to the terminals). The connections of the terminals to the electrodes of the lead system of FIG. 1 have been previously described.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses. The pacing stimulation pulses are made available as required at terminal 43 ($A_R$ TIP), terminal 44 ($A_R$ RING), terminal 47 ($V_R$ TIP), terminal 48 ($V_R$ RING), terminal 51 ($A_L$ TIP), terminal 52 ($A_L$ RING), terminal 55 ($V_L$ TIP) and terminal 56 ($V_L$ RING). The device is thus capable of providing stimulation pacing pulses for use in each of the four chambers of the heart. The atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control 10 circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to appropriate ones of the terminals for connection to corresponding lead electrodes for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 may be coupled to any combination of the terminals 42–44, 46–48, 50–52, and 54–56 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

The stimulation device 10 may further include a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. The type of sensor used is not critical to the present invention and is shown only for completeness.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown for example in FIG. 1, selected from the left atrial coil electrode 548, the left ventricular coil electrode 544, the SVC coil electrode 558, and the right ventricular coil electrode 536. As noted above, the housing 40 may act as a return electrode in combination with any one of the electrodes, or any combination of the electrodes for example, as part of a split electrical vector using the SVC coil electrode 558 or the left atrial coil electrode 548 (i.e., using the RV coil electrode 536 as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation system for delivering stimulation pulses to any one chamber or combination of chambers of a heart, the system comprising:

a lead system consisting of a first lead for implant in the right ventricle and having a right ventricular defibrillation electrode, a second lead for implant in the coronary sinus and having a left ventricular defibrillation electrode for placement in electrical contact with the left ventricle adjacent to the left ventricle and within the coronary sinus and a first left ventricular pacing electrode for placement in electrical contact with the left ventricle and within the coronary sinus and a second left ventricular pacing electrode proximal to the first left ventricular pacing electrode for placement in electrical contact with the left ventricle, and a third lead for implant in the coronary sinus and having a left atrial defibrillation electrode for placement in electrical contact with the left atrium adjacent to the left atrium and within the coronary sinus, one of the leads further including a right atrial defibrillation electrode for placement in one of the right atrium and superior vena cava; and an implantable cardiac stimulation device including a programmable pulse generator that delivers defibrillation pulses to the defibrillation electrodes.

2. The system of claim 1 wherein the right atrial defibrillation electrode is carried on the third lead.

3. The system of claim 2 wherein the first lead further includes a first right ventricular pacing electrode and wherein the pulse generator is programmable to deliver pacing pulses to the first right ventricular pacing electrode.

4. The system of claim 3 wherein the first lead further includes a second right ventricular pacing electrode proximal to the first right ventricular pacing electrode and wherein the pulse generator is programmable to deliver pacing pulses between the first right ventricle pacing electrode and the second right ventricular pacing electrode.

5. The system of claim 2 wherein the pulse generator is programmable to deliver pacing pulses to the first left ventricular pacing electrode.

6. The system of claim 5 wherein the pulse generator is programmable to deliver pacing pulses between the first left ventricle pacing electrode and the second left ventricular pacing electrode.

7. The system of claim 2 wherein the third lead further includes a first left atrial pacing electrode for placement in electrical contact with the left atrium and wherein the pulse generator is programmable to deliver pacing pulses to the first left atrial pacing electrode.

8. The system of claim 7 wherein the third lead further includes a first right atrial pacing electrode for placement in electrical contact with the right atrium, and wherein the pulse generator is programmable to deliver pacing pulses to either one or both of the atrial pacing electrodes.

9. The system of claim 8 wherein the atrial pacing electrodes are spaced apart on the lead body so that when the first left atrial pacing electrode is in electrical contact with and adjacent the left atrium within the coronary sinus, the first right atrial pacing electrode is in electrical contact with the right atrium and adjacent to the ostium of the coronary sinus within the coronary sinus.

10. The system of claim 8 wherein the third lead further includes a second right atrial pacing electrode, the second right atrial pacing electrode distal to the first right atrial pacing electrode, and wherein the pulse generator is programmable to deliver pacing pulses between the first right atrial pacing electrode and the second right atrial pacing electrode.

11. The system of claim 7 wherein the left atrial defibrillation electrode is proximal to the first left atrial pacing electrode on the third lead.

12. The system of claim 11 wherein the third lead further includes a second left atrial pacing electrode proximal to the left atrial defibrillation electrode for placement in electrical contact with the left atrium, and wherein the pulse generator is programmable to deliver pacing pulses to the second left atrial pacing electrode.

13. The system of claim 2 wherein the defibrillation electrodes are coil electrodes.

14. The system of claim 2 wherein the device includes a conductive case and wherein the pulse generator is programmable to deliver stimulation pulses between any one of the defibrillation electrodes and the case.

15. The system lead of claim 8 wherein the left atrial difibrillation electrode is proximal to the first left atrial pacing electrode, wherein the third lead further includes a second left atrial pacing electrode proximal to the left atrial difibrillation electrode for placement in electrical contact with the left atrium, and a second and right atrial pacing electrode distal to the first right atrial pacing electrode for placement in electrical contact with the right atrium, and wherein the pulse generator delivers defibrillation stimulation pulses to the left atrial defibrillation electrode, right atrial pacing pulses to any one or both of the right atrial pacing electrodes, and left atrial pacing pulses to any one or both of the left atrial pacing electrodes.

16. The system of claim 15 wherein the defibrillation electrodes are coil electrodes.

17. The system of claim 15 wherein the device includes a conductive case and wherein the pulse generator delivers defibrillation stimulation pulses between any one of the defibrillation electrodes and the case and is programmable to deliver pacing pulses between any one of the pacing electrodes and the case.

* * * * *